United States Patent [19]

Ratcliffe

[11] 4,287,128

[45] Sep. 1, 1981

[54] PROCESS FOR PREPARING EPOXIDES

[75] Inventor: Charles T. Ratcliffe, Morristown, N.J.

[73] Assignee: Allied Corporation, Morris Township, Morris County, N.J.

[21] Appl. No.: 141,550

[22] Filed: Apr. 18, 1980

Related U.S. Application Data

[62] Division of Ser. No. 50,585, Jun. 21, 1979, abandoned.

[51] Int. Cl.$^3$ .................. C07D 301/03; C07D 273/01
[52] U.S. Cl. .............................. 260/348.23; 260/333; 260/348.48
[58] Field of Search ........................... 260/333, 348.23

[56] References Cited

U.S. PATENT DOCUMENTS 3,358,003  12/1967  Eleuterio et al. ............... 260/348.31

FOREIGN PATENT DOCUMENTS 904877  9/1962  United Kingdom ................ 260/348.31

OTHER PUBLICATIONS

E. R. Falardeau et al., Jour. Am. Chem. Soc., vol. 98, No. 12 (1976) pp. 3529-3533.

Primary Examiner—Norma S. Milestone

[57] ABSTRACT

A new process for preparing haloalkyl epoxides and oxaziranes is described in which a mixture of an perhalo alkene or alkyl imine and chlorine gas is contacted with a Group IA, IIA metal oxide, carbonate or bicarbonate under mild conditions of temperature and pressure. The process, using perhalo alkenes or perhalo alkyl imines as starting material, represents a new economical, facil preparation of the monomer hexafluoropropylene oxide, such monomer is capable of polymerizaton or copolymerization to thermally stable and inert polymers.

3 Claims, No Drawings

PROCESS FOR PREPARING EPOXIDES

This is a division, of application Ser. No. 050,585, filed June 21, 1979 abandoned.

DESCRIPTION

BACKGROUND OF THE INVENTION

1. Field of the Invention

This invention relates to a process for preparing perhaloalkyl epoxides and oxaziranes by contacting a mixture of a perhalogenated alkene or alkyl imine and chlorine gas with a Group IA, IIA metal oxide, carbonate or bicarbonate under mild conditions of temperature and pressure.

2. Brief Description of the Prior Art

Perhaloalkyl epoxides, particularly perfluoroalkyl epoxides are useful as monomer in forming polyfluorinated ethers useful as high temperature lubricants. An especially useful perfluoroalkyl epoxide in this regard is the known hexafluoropropylene oxide.

Perhaloalkyl oxaziranes are a little known class of organic compounds. The simplest member of the perfluorinated family,

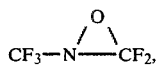

is described without indication of any use for such member by Falardeau and Des Marteau in J. Am. Chem. Soc. 98, pp. 3529-3522 (1976).

Eleuterio et al. in U.S. Pat. No. 3,358,003 disclose preparation of fluorocarbon epoxides in alkaline aqueous solution of an inorganic peroxide or of sodium hypchlorite.

Similarly, British Pat. No. 904,877 discloses reaction of fluorocarbons with an alkaline aqueous solution of an inorganic peroxide.

SUMMARY OF THE INVENTION

According to the present invention, a process for epoxidation of perhaloolefines and/or perhaloalkyl imines is disclosed.

The starting materials of perhaloolefines and/or perhaloalkyl imines are contacted with one or more members of the group consisting of the carbonates, bicarbonates and oxides of the alkali and alkaline earth metals in the presence of elemental chlorine and an effective amount of moisture. Epoxides of the perhaloolefinic and/or perhaloalkyl imines are obtained such as compounds of the formula

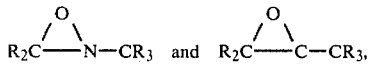

respectively, wherein each R is independently fluorine or $C_1$-$C_{20}$ perhalogenated alkyl radical with the halogen being fluorine, chlorine or mixtures thereof with the proviso in the case of the perhaloalkyl imines that no more than four R are fluorine and that at least one R connects through a difluoro methylene grouping.

The epoxides prepared according to the present invention are useful as polymerizable monomers for yielding lubricating oils, hydraulic fluids, and temperature stable and corrosion resistant polymers.

DETAILED DESCRIPTION OF THE PREFERRED EMBODIMENTS

According to the present invention, a method is disclosed for preparing halogenated epoxides and halogenated oxaziranes from the corresponding haloolefins and halogenated azaolefins, respectively, wherein halogen is fluorine, chlorine or mixtures thereof. The method of preparation for the above compounds consists of the interaction of an alkali metal or alkaline earth carbonate, bicarbonate or oxide, an effective amount of moisture and elemental chlorine on the unsaturated linkage of the perhaloalkene, or perhaloazaalkene. The following equations show this for an alkali metal carbonate by way of example.

(a) $M_2CO_3 + Cl_2 + CF_3CF=CF_2 \longrightarrow$

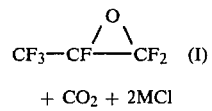

$+ CO_2 + 2MCl$ (b) $M_2CO_3 + Cl_2 + i\text{-}C_3F_7-N=C(CF_3)_2 \longrightarrow$

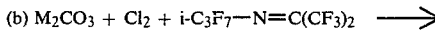
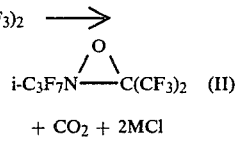

$+ CO_2 + 2MCl$

M = Na, K, Cs, Rb

Starting materials include perhaloolefines and/or perhalo alkyl imines, wherein the halogen is fluorine or chlorine or mixtures thereof.

Preferred perhaloolefines include compounds of the formula $R_2C=CF-CR_3$ wherein each R is, independently fluorine or a $C_1$-$C_{20}$ perhalogenated alkyl radical and halogen being fluorine, chlorine or mixtures thereof. More preferred perhaloolefines have R=fluorine or a $C_1$-$C_{10}$ perhalogenated alkyl. Examples of the perhaloolefins include: perfluoropropene, perfluorobutene-2, and chloroperfluoropropene. Preferred perhaloalkyl imines include compounds of the formula $R_2C=N-CR_3$ wherein R is fluorine or a $C_1$-$C_{20}$ perhalogenated alkyl radical and halogen being fluorine, chlorine or mixtures thereof with the proviso that no more than four of the R are fluorine. More preferred perhaloalkyl imines includes those wherein R is fluorine or a $C_1$-$C_{10}$ perhalogenated alkyl radical.

Preferred perhalo imine starting materials have the formula $R_2C=N-CR_3$ wherein each R is independently fluorine or a $C_1$-$C_{10}$ perhalogenated alkyl radical with the halogen being fluorine, chlorine or mixtures thereof with the proviso that no more than four of the R's are fluorine and that at least one R radical connects through a difluoro methylene grouping.

Examples of the perhaloalkyl imines include perfluoro-2,4-dimethyl-3-aza pentene, perfluoro-2-methyl, 3-aza hexene, perfluoro-2-methyl, 4-chloro-3-aza hexene.

Starting materials can be prepared by conventional methods. Such materials are disclosed in Organic Fluorine Chemistry, W. A. Sheppard and C. M. Sharts, W. A. Benjamin Inc., 1969 and by C. Woolf et al., Fifth International Symposium on Fluorine Chemistry, Moscow, Soviet Union, 1971.

The reaction is generally carried out at ambient or near ambient temperatures by allowing chlorine and the olefin to contact the alkali metal salt and/or alkaline earth metal carbonate, bicarbonate and/or oxide in a contained system. Such system can be made from a material inert to the reactants such as glass, silver etc. The reaction temperature can be from about $-20°$ C. to $100°$ C. The reaction rate increases with increased ionic size of the alkali metal and is generally complete within a few minutes at room temperature for $Cs_2CO_3$. The contacting time is not limited, but preferred times are between two minutes and ten hours. The contacting time depends on the starting compound, the nature of the alkaline metal or alkaline earth metal carbonate, bicarbonate or oxide, the stoichiometric conditions, the reaction configuration and the reaction temperature. A trace amount of moisture is necessary to catalyze the above reaction. The moisture content of commercial alkali metal carbonates is sufficient to effect this catalysis.

The desired product from equation (a) or (b) is in many cases volatile and can be pumped out of the reaction vessel as a gas. Purification of the fluorooxazirane (II) from the byproduct carbon dioxide can readily be achieved by pumping off the latter under vacuum from a vessel containing the mixture at $-78°$ C.

Perfluoropropene oxide (I), which contains unreacted perfluoropropene, can be recycled before purification. Carbon dioxide can be removed by trap-to-trap distillation or directly adsorbed on cesium oxide in the reaction vessel.

The reaction of the present invention is a selective one. E.g., tetrafluoroethylene and $CF_3-N=CF_2$ do not form epoxides when subjected to the process of the present invention.

Excess chlorine can be separated from the reaction product by condensation. The perhalogenated epoxides are useful as electrophilic and nucleophilic coupling agents and as intermediates for preparation of polymers and of lubricants.

The epoxides prepared according to the present invention can be cleaved, involving a nucleopholic substitution of the epoxide oxygen by an alkyl carbanion generated from an alkyl magnesium halide. Hydrolysis of the intermediate alkoxide yields an alcohol.

The epoxide may also be cleaved by water in the presence of mineral acid to yield glycols, but only resultant tertiary perfluoro alcohols are stable. Secondary perfluoro alcohols would be subject to decomposition into hydrofluoric acid and an aldehyde.

The epoxides can be polymerized to perhalogenated polyolefinoxides, are useful as high temperature lubricating oils, hydraulic fluids and the like. Solid polymers of these epoxides have properties similar to polytetrafluorethylene and exhibit temperature stability and corrosion resistance.

The oxazirane can be hydrolyzed to aldehydes and $\beta$-alkylhydroxylamines. Alternatively, the oxaziranes can be thermally isomerized under anhydrous conditions to nitrones.

The oxaziranes can form complexes with transition metal ions such as ferric ion. Such complexes catalyze the photopolymerization of unsaturated ethylenic monomers.

The oxaziranes of the present invention are useful as catalysts for alcoholysis and phenolysis with phosphorus pentasulfide.

The oxaziranes furthermore can polymerize or copolymerize to liquids and solids having high thermal stabilities (up to about $400°$ C.) and high chemical inertness comparable to that of polytetrafluoroethylene.

EXAMPLE 1

Preparation of 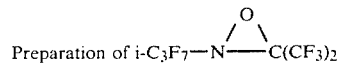

A 25 gram sample of $Cs_2CO_3$ obtained from Alpha Inorganic was placed in a 3 oz. aerosol compatibility tube. After the tube was evacuated and cooled to $-196°$ C., 10 mmole samples of $i-C_3F_7N=C(CF_3)_2$ and chlorine were condensed onto the salt. The mixture was allowed to warm to ambient temperature for 3 hours. Analysis of the volatile products revealed no starting material, with $CO_2$ and

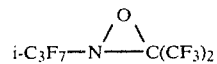

as the only products. When the product mixture was contained in a cold trap at $-78°$ C. and submitted to dynamic vacuum, the $CO_2$ was effectively pumped off leaving a pure sample of the fluorooxazirane,

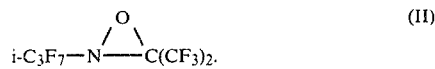

Mass balance of the reaction showed near quantitative yield of the oxazirane (II) with less than stoichiometric amounts of $CO_2$. The weight increase in the residue salt accounted for the remaining molar amount of $CO_2$.

The fluorooxazirane (II) revealed a loss of the $C=N$ stretching frequency in the infrared spectrum. High resolution mass spectrum of the sample gave a parent ion and cracking pattern in agreement with the above structure. When a sample was injected through a high temperature inlet a different cracking pattern containing the same parent ion was observed. This spectrum was believed to be due to the isomer

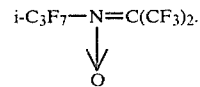

The $F^{19}$ NMR spectrum gave five resonance peaks with extensive hyperfine splitting. Chemical shifts and ratios of the above resonances agreed with four $CF_3$ groups and one CF group.

Elemental Analysis for $C_6F_{13}NO$:
Calc: %C, 20.63; %F, 70.77; %N, 4.01.
Found: %C, 20.15; %F, 69.06; % N, 4.47.

EXAMPLE 2

Preparation of 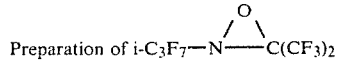

A 10 gram sample of $K_2CO_3$ was added to a dry 3 oz. aerosol tube. After the tube was evacuated and cooled to $-196°$ C., equimolar samples (4 mmoles) of $Cl_2$ and $i-C_3F_7-N=C(CF_3)_2$ were condensed onto the salt by standard vacuum line technique. The volatile products were checked after 20 min. at ambient temperature and revealed approximately 80% conversion to the desired fluorooxazirane. An addition of a 2 mmole sample of chlorine was condensed into the reaction mixture and the vessel was held at ambient temperature for 24 hours. Analysis of the product mixture revealed near quantitative yield of

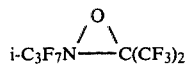

with complete conversion. The product was identified by comparison of its infrared spectrum with a known sample.

EXAMPLE 3

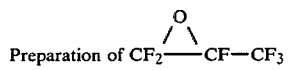

A 25 gram sample of $Cs_2CO_3$ obtained from Alpha Inorganic was contained in a dry 3 oz. aerosol tube and evacuated for 15 min. After 14 mmole samples of $Cl_2$ and $C_3F_6$ had been condensed into the vessel at $-196°$ C., the vessel was slowly warmed to room temperature. The interaction of $Cl_2$ was observed to occur at below room temperature with no yellow color apparent by the time the vessel had reached ambient temperature. A pressure reading of 60 psi was observed at ambient temperature followed by an exothermic reaction and pressure decrease. Analysis of the volatile products revealed only $C_3F_6$ and $C_3F_6O$. The secondary exothermic reaction apparently involved the readsorption of $CO_2$ by the salt. Gas chromatographic analysis of the product mixture gave 95.8% yield of $C_3F_6O$. Resolution of the peaks corresponding to $C_3F_6$ and $C_3F_6O$ was not complete but the conversion was estimated to be 30–50%. Mass spectrum and infrared spectrum of the product confirmed the presence of $C_3F_6O$ and $C_3F_6$ as the two components.

EXAMPLE 4

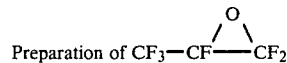

An equimolar mixture of $Cl_2$ and $C_3F_6$ was condensed into an evacuated aerosol tube containing 15 grams of $K_2CO_3$. After 30 hours at ambient temperature under dark conditions, the volatile products were removed and analyzed by gas chromatography. Equal quantities of $C_3F_6O$ and $C_3F_6Cl_2$ were observed with approximately 20% conversion of $C_3F_6$. Carbon dioxide represented the only other volatile product.

I claim:

1. A process of epoxidation of perhalo olefins of the formula $R_2C=CFCR_3$ wherein each R is independently fluorine and/or a $C_1$–$C_{10}$ perhalogenated alkyl radical with the halogen being fluorine, chlorine or mixtures thereof, comprising: contacting said perhalo olefin with at least one member of the group consisting of the carbonates, bicarbonates and oxides of the alkali and alkaline earth metals in presence of elementary chlorine and an effective amount of moisture.

2. The method of claim 1 wherein said perhalo olefin is a perfluoro compound and is contacted at temperature in the range of $-20°$ to $100°$ C. with at least one alkali metal carbonate of the group consisting of cesium carbonate and potassium carbonate.

3. Method of claim 2 wherein said perfluoro compound is hexafluoropropene and said carbonate is cesium carbonate.

* * * * *